United States Patent [19]
Wortel

[11] Patent Number: 4,701,315
[45] Date of Patent: * Oct. 20, 1987

[54] ZEOLITE L AND PROCESS FOR ITS PREPARATION

[75] Inventor: Theodorus M. Wortel, Houston, Tex.

[73] Assignee: Exxon Research & Engineering Co., Florham Park, N.J.

[*] Notice: The portion of the term of this patent subsequent to Oct. 1, 2002 has been disclaimed.

[21] Appl. No.: 724,672

[22] Filed: Apr. 18, 1985

Related U.S. Application Data

[63] Continuation of Ser. No. 493,688, May 11, 1983, Pat. No. 4,544,539.

[30] Foreign Application Priority Data

May 14, 1982 [GB] United Kingdom ................. 8214147

[51] Int. Cl.$^4$ ............................................. C01B 33/28
[52] U.S. Cl. .................................. 423/328; 423/329; 423/330; 423/331; 502/60; 502/66
[58] Field of Search ............................. 423/328–331; 502/60, 66

[56] References Cited

U.S. PATENT DOCUMENTS

| | | | |
|---|---|---|---|
| 3,216,789 | 1/1965 | Breck et al. ............................. | 23/113 |
| 3,298,780 | 1/1967 | Fleck ....................................... | 423/329 |
| 3,794,600 | 2/1974 | Schutt ............................. | 252/455 Z |
| 3,867,512 | 2/1975 | Young ..................................... | 423/329 |
| 4,104,320 | 8/1978 | Bernard et al. .................... | 260/673.5 |
| 4,416,806 | 11/1983 | Bernard et al. ......................... | 502/74 |
| 4,417,083 | 11/1983 | Bernard et al. ....................... | 585/419 |
| 4,552,856 | 11/1985 | Tauster et al. ......................... | 502/66 |
| 4,594,145 | 6/1986 | Roarty .................................... | 208/133 |
| 4,595,668 | 6/1986 | Poeppelneir et al. ................. | 502/66 |
| 4,595,669 | 6/1986 | Fung et al. ............................. | 502/74 |
| 4,595,670 | 6/1986 | Tausler et al. .......................... | 502/66 |

FOREIGN PATENT DOCUMENTS

| | | |
|---|---|---|
| 888365 | 4/1981 | Belgium . |
| 0026963 | 4/1981 | European Pat. Off. . |
| 0031255 | 7/1981 | European Pat. Off. . |
| 0040119 | 11/1981 | European Pat. Off. . |
| 88789 | 3/1972 | German Democratic Rep. . |
| 1202511 | 5/1970 | United Kingdom . |
| 1393365 | 7/1975 | United Kingdom . |

OTHER PUBLICATIONS

L. Wilkosz, Synthesis Type L Zeolite, 12/1/75; Uniwersytetu Jagiellonskiego, Chem. Abstracts, vol. 90, 57347F.

G. V. Tsitsishvili et al., Synthesis and Crystallization Kinetics of Zeolite L, in Doklady Akademii Nauk SSR, vol. 243, No. 2, pp. 438–440, (1978).

Y. Nishimura, Synthesis and Physico-Chemical Properties of Zeolite L, in Nippon Kagaku Zasshi 91, 11, (1970), pp. 1046–1049.

Frety et al., Examination By Electronic Microscope of the Pore Structure of Type L Zeolite, in C. R. Acad. Sc. Paris, t. 275, (11/1975), Serie C–1215.

L. Wilkosz, Synthesis of Zeolite L, (1974), Zeszyty Naukowe Uniwersytetu Jagiellonskiego, pp. 409–418.

Primary Examiner—John Doll
Assistant Examiner—Jackson Leeds
Attorney, Agent, or Firm—M. D. Bittman; E. T. Wheelock

[57] ABSTRACT

A zeolite related to zeolite L and having a characteristic cylindrical morphology may be prepared from a crystallization gel comprising (in mole ratios of oxides):

$K_2O/SiO_2$—0.22–0.36
$H_2O/K_2O$—25–90
$SiO_2/Al_2O_3$—6–15 and preferably with the mole ratio $H_2O/K_2O+Al_2O_3+SiO_2$ being at least 8. The cylindrical Zeolite L may be used as a catalyst base in aromatization of acyclic hydrocarbons with high benzene yields being sustained over commerically feasible periods.

27 Claims, 5 Drawing Figures

ZEOLITE L AND PROCESS FOR ITS PREPARATION

This is a continuation of application Ser. No. 493,688 filed May 11, 1983, now U.S. Pat. No. 4,544,539.

This invention relates to a highly crystalline zeolite material, its preparation and use in catalysis, particularly for aromatization. In particular it relates zeolite L with cylindrical morphology.

Zeolite L has been known for some time as an adsorbant, and in U.S. Pat. No. 3,216,789 is described as an aluminosilicate of the formula:

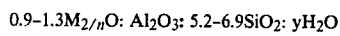

$$0.9-1.3M_{2/n}O: Al_2O_3: 5.2-6.9SiO_2: yH_2O$$

(where M is an exchangeable cation of valence n and y is from 0 to 9) having an X-ray diffraction pattern with the following more significant d (Å) values:

16.1±0.3
7.52±0.04
6.00±0.04
4.57±0.04
4.35±0.04
3.91±0.02
3.47±0.02
3.28±0.02
3.17±0.01
3.07±0.01
2.91±0.01
2.65±0.01
2.46±0.01
2.42±0.01
2.19±0.01

The preparation of zeolite L described in U.S. Pat. No. 3,216,789 comprises crystallizing the zeolite from a reaction mixture comprising mole ratios:

$K_2O/(K_2O+Na_2O)$—0.33-1
$(K_2O+Na_2O)/SiO_2$—0.35-0.5
$SiO_2/Al_2O_3$—10-28
$H_2O/(K_2O+Na_2O)$—15-41

The silica to alumina ratio in this reaction mixture is significantly higher than the ratio in the formed zeolite.

British Pat. No. 1 202 511 describes a revised zeolite L preparation using lower proportions of silica in the reaction mixture which comprises mole ratio of reactants as:

$K_2O/(K_2O+Na_2O)$—0.7-1
$(K_2O+Na_2O)/SiO_2$—0.23-0.35
$SiO_2/Al_2O_3$—6.7-9.5
$H_2O/(K_2O+Na_2O)$—10.5-50

The ratio $H_2O/(K_2O+Na_2O+SiO_2+Al_2O_3)$ is preferably not greater than 6 to give a "dry gel".

U.S. Pat. No. 3,867,512 discloses a preparation of zeolite L from a reaction mixture having a molar composition:

$K_2O/(K_2O+Na_2O)$—0.3-1
$(K_2O+Na_2O)/SiO_2$—0.3-0.6
$SiO_2/Al_2O_3$—10-40
$H_2O/(K_2O+Na_2O)$—15-140 in which the silica source is a gel having at least 4.5 weight percent water and prepared in a particular manner.

L Wilkosz in Pr Chem 409 (1974)—Chemical Abstracts, vol 90 (1979) 573478 describes the preparation of zeolite L from a synthesis sol prepared by treating a solution containing silica, potassium hydroxide and sodium hydroxide with a second solution containing potassium aluminate, potassium hydroxide and sodium hydroxide and crystallizing for 72 hours at 20° C. and 122 hours at 100° C. The zeolite L product has a $SiO_2:Al_2O_3$ ratio of 6.4:1.

G V Tsitsishvilli et al in Doklady Akademii NaukSSSR, Vol 243, No 2, pp 438-440 (1978) describe the synthesis of zeolite L from alumina-silica gels containing tributylamine. The gels used had the following molar ratios:

$SiO_2:Al_2O_3$—25
$(K_2O+Na_2O):Al_2O_3$—18
$(K_2O+Na_2O):SiO_2$—0.72
$H_2O/K_2O+Na_2O$—20
$K_2O:Na_2O$—0.5

Y Nishiimura in Nippon Kagaku Zasshi 91, 11, 1970, pp 1046-9 describes in general terms zeolite L preparation from a synthesis mixture containing colloidal silica, potassium aluminate and potassium hydroxide having a $SiO_2:Al_2O_3$ ratio of 15-25, but exemplifies only two synthesis mixtures having the following ratios of components:

$7K_2O:Al_2O_3:20SiO_2:450H_2O$; and
$8K_2O:Al_2O_3:10SiO_2:500H_2O$.

Frety et al in C R Acad Sc Paris, t275, Serie C-1215 describes the electron microscope examination of zeolite L in which particles were said to be observed in the form of slightly deformed cylinders with very variable dimensions.

U.S. Pat. No. 3,298,780 describes zeolite UJ having a composition, expressed as mole ratios of oxides, corresponding to

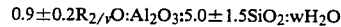

$$0.9\pm0.2R_{2/\nu}O:Al_2O_3:5.0\pm1.5SiO_2:wH_2O$$

wherein R represents at least one cation having a valence of not more than 4, v represents the valence of R and w can be any value up to about 5, said zeolite having an X-ray powder diffraction pattern essentially as shown in the following table:

| Interplanar spacing, d (Å) | Relative Intensity |
|---|---|
| 16.25 ± 0.25 | VS |
| 7.55 ± 0.15 | M |
| 6.50 ± 0.10 | M |
| 5.91 ± 0.10 | W |
| 4.61 ± 0.05 | S |
| 3.93 ± 0.05 | S |
| 3.67 ± 0.05 | W |
| 3.49 ± 0.05 | M |
| 3.29 ± 0.05 | W |
| 3.19 ± 0.05 | M |
| 3.07 ± 0.05 | M |
| 2.92 ± 0.05 | M |
| 2.66 ± 0.05 | W | prepared by a process comprising preparing an aqueous reactant solution having a composition, expressed as mole ratios of oxides, corresponding to $SiO_2/Al_2O_3$ of from 6 to 30,
$R_{2/\nu}O/SiO_2$ of from 0.30 to 0.70, and
$H_2O/R_{2/\nu}O$ of from 80 to 140; and maintaining said reactant solution at a temperature between 150° F. (65.6° C.) and 325° F. (162.8° C.) until the zeolite crystals are formed. Zeolite UJ is described as having nearly cubic shaped crystals with a crystal size ranging upward from 0.05 micron.

GB No. 1 393 365 described zeolte AG1, related to zeolite L, having the molar composition other than water:

$1.05\pm0.3M_2O:Al_2O_3:4.0-7.5SiO_2$ wherein M is potassium or a mixture of potassium and sodium, and an X-ray powder diffraction pattern substantially as set forth in Columns I and II of the following table, and capable of adsorbing at least 3% w/w perfluorotributylamine.

| COLUMN I Potassium zeolite AG1 | | COLUMN II Potassium/sodium zeolite AG1 | |
|---|---|---|---|
| d(A) | Relative intensity | d(A) | Relative Intensity |
| 15.85 | 36.9 | 15.78 | 37.5 |
| — | — | — | — |
| 7.53 | 8.5 | 7.50 | 10 |
| 6.00 | 9.5 | 6.00 | 10 |
| — | — | 5.86 | 7 |
| 5.75 | 6 | — | — |
| 4.61 | 24 | 4.59 | 28 |
| 4.40 | 7 | 4.40 | 7 |
| 4.35 | 5 | — | — |
| 3.93 | 31 | 3.91 | 35 |
| — | — | — | — |
| 3.66 | 13 | 3.65 | 17 |
| 3.48 | 17 | 3.47 | 23 |
| 3.27 | 13 | 3.27 | 17 |
| 3.186 | 29 | 3.18 | 31.5 |
| 3.07 | 20 | 3.07 | 24 |
| 3.01 | 9.5 | — | — |
| 2.91 | 21.5 | 2.91 | 28 |
| 2.65 | 15.5 | 2.65 | 18.5 |
| — | — | — | — |
| — | — | 2.50 | 6 |
| 2.49 | 5 | — | — |
| 2.46 | 3 | 2.46 | 5 |
| 2.42 | 3 | 2.42 | 4 |
| 2.19 | 8 | 2.19 | 12 |

Zeolite AG1 is described as being prepared by reacting at least one aluminium component, at least one silicon component and at least one alkali metal component, in an aqueous medium, the sole or major silicon component being a water glass having a molar ratio $SiO_2/M_2O$ of 3.5 to 4.0 to give a reaction mixture with oxide molar ratios in one of the following ranges:

| Range 1 | $SiO_2/Al_2O_3$ | 7–14 |
|---|---|---|
| | $(K_2O + Na_2O)/SiO_2$ | 0.25–0.85 |
| | $K_2O/(K_2O + Na_2O)$ | 0.75–1.0 |
| | $H_2O/(K_2O + Na_2O)$ | 25–160 |
| Range 2 | $SiO_2/Al_2O_3$ | 14–20 |
| | $(K_2O + Na_2O)/SiO_2$ | 0.25–0.85 |
| | $K_2O/(K_2O + Na_2O)$ | 0.5–1.0 |
| | $H_2O/(K_2O + Na_2O)$ | 25–160 |
| Range 3 | $SiO_2/Al_2O_3$ | 20–40 |
| | $(K_2O + Na_2O)/SiO_2$ | 0.25–1.0 |
| | $K_2O/(K_2O + Na_2O)$ | 0.4–1.0 |
| | $H_2O/(K_2O + Na_2O)$ | 25–160 |

It was subsequently found that zeolite L may be used as a catalyst base in aromatization reactions. U.S. Pat. No. 4,104,320 discloses dehydrocyclization of aliphatic compounds in the presence of hydrogen using a catalyst comprising zeolite L and a group VIII metal, in which the zeolite L is of the formula:

$$M_{9/n}(AlO_2)_9(SiO_2)_{27}$$

(where M is a cation of valence n) but the silica to alumina ratio may vary from 5 to 7. Zeolite L is described as occuring in the form of cylindrical crystals a few hundred Angstroms in diameter.

East German Patent No. 88789 discloses dehydrocyclization using a catalyst formed from a zeolite precursor with a silica to alumina ratio of 5 or greater which is dealuminised to give a silica to alumina ratio of up to 70. Zeolite L is mentioned as a precursor.

European Patent Application Publication No. 40119 discloses a dehydrocyclization process operating at low pressure (1 to 7 bars) or low $H_2$/hydrocarbon ratio using a catalyst comprising platinum on a potassium zeolite L. BE 888365 describes dehydrocyclization using a catalyst comprising platinum, rhenium (incorporated in the form of its carbonyl) and sulphur to give an atomic ratio of sulphur to platinum of 0.05 to 0.6 on a zeolitic crystalline aluminosilicate base such as zeolite L. BE 792608 discloses the treatment of zeolite L for use as catalyst in isomerization by exchange with ammonium and chromium ions.

It has now been found that a new zeolitic material having some similar characteristics to zeolite L, but having a characteristic morphology and size is particularly valuable for use as a catalyst base in hydrocarbon conversions such as aromatization.

Figure 1:
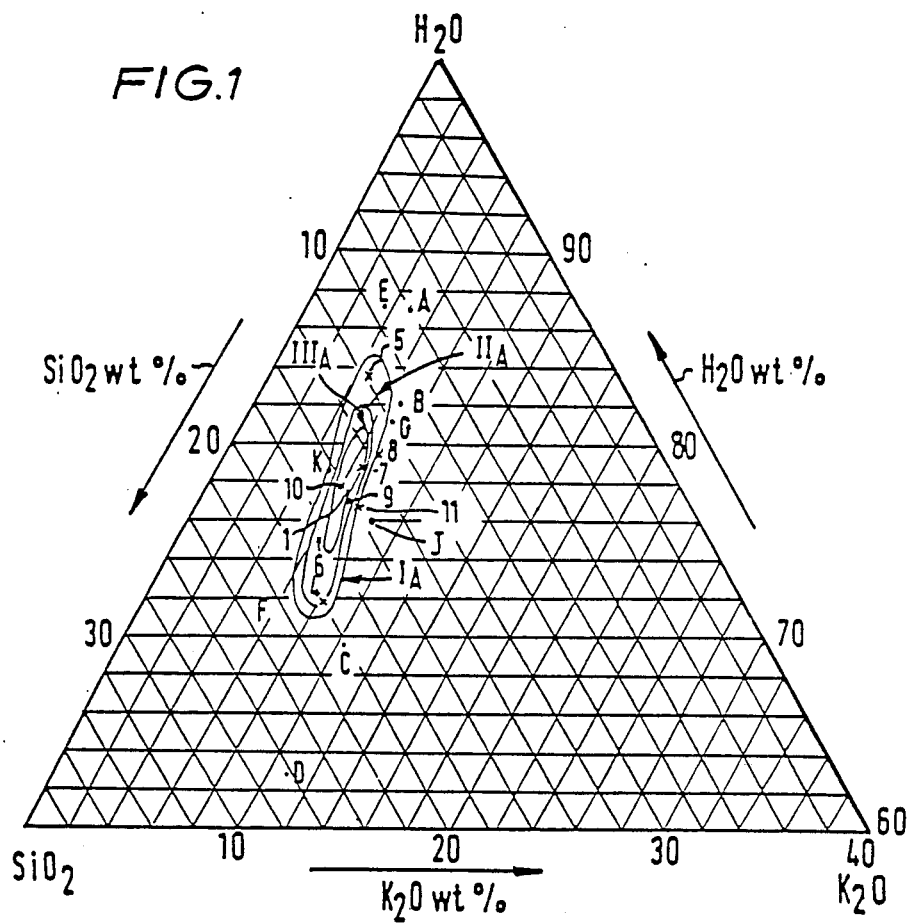
FIGS. 1–4 are triangular graphs showing the preferred proportions of the components in the synthesis gel used in producing zeolite L.

Thus, in one aspect this invention concerns a zeolite having an X-ray diffraction (XRD) pattern obtained with CuKα radiation having the following significant d (Å) values:

TABLE A 16.1±0.4
7.52±0.05
6.00±0.04
4.57±0.04
4.35±0.04
3.91±0.02
3.47∓0.02
3.28±0.02
3.17±0.02
3.07±0.02
2.91±0.02
2.65±0.02
2.46±0.02
2.42±0.01
2.19±0.01 and comprising crystallites in the form of cylinders with a mean diameter of at least 0.1 micron. The above XRD lines characterize the zeolite of the invention and correspond to those identified as characteristic of zeolite L in U.S. Pat. No. 3,216,789. The spectrum of the zeolite of the invention will also generally show additional lines, and more complete listings of the d (Å) values for specific materials of the invention are given hereinafter. In general the ten most prominent peaks in the XRD pattern of the materials of the invention are given in Table B below:

TABLE B 16.1±0.4
4.57±0.04

3.91±0.02
3.66±0.02
3.47±0.02
3.28±0.02
3.17±0.02
3.07±0.02
2.91±0.02
2.65±0.02

The positions and relative intensities of the X-ray lines are found to vary only slightly with changes in the cation form of the materials. However, the intensity of the line at d=16.1±0.3 Å has been observed to be more variable than that of other prominent lines. This is believed to be a result of the sensitivity of this peak to the preparation of the XRD sample and not to significant changes in crystal structure of the zeolite. Occasionally, additional lines not belonging to the pattern for zeolite L appear in a pattern along with the X-ray lines characteristic of the zeolite. This is an indication that one or more additional crystalline materials are mixed with zeolite L in the sample being tested. It is a preferred feature of the invention that the amount of such additional crystalline materials is minimised in the zeolite material as synthesized. In particular, as discussed in more detail hereinafter, it is preferred that the synthesis of the zeolite of the invention is conducted so that the amount of zeolite W in the product of the synthesis is minimised. Further, the synthesis of the zeolite of the invention is preferably conducted such that the product of the synthesis is substantially free of any additional crystalline phase giving rise to a line in the X-ray pattern at d (Å) value of 6.28±0.05.

The particular X-ray technique and/or apparatus employed, the humidity, the temperature, the orientation of the crystals in the sample and other variables, all of which are well known and understood to those skilled in the art of X-ray crystallography or diffraction, may also cause some variations in the positions and intensities of the X-ray lines. Thus, the X-ray data given herein to identify the zeolites of the invention are not to exclude those materials which, due to some variable mentioned above or otherwise known to those skilled in the art fail to show all of the tabulated X-ray lines, or show a few extra ones that are permissible to the crystal system of the zeolite, or show a shift in position or slight change in intensity of some of the X-ray lines.

The zeolites of the invention are preferably aluminosilicates and will be described hereinafter in terms of aluminosilicates, though other elemental substitutions are possible, for example aluminium may be substituted by gallium, boron, iron and similar trivalent elements, and silicon may be substituted by elements such as germanium or phosphorus. The aluminosilicates preferably have a composition (expressed in terms of molar ratios of the constituent oxides in anhydrous form) of:

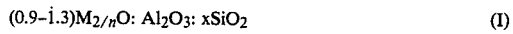

$(0.9–1.3)M_{2/n}O: Al_2O_3: xSiO_2$      (I)

wherein M is a cation of valence n, x is from 5 to 7.5, preferably from about 5.7 to about 7.4. The zeolitic materials of the invention have high crystallinity as shown by a well-defined X-ray diffraction pattern (without binder or other diluents present) with sharp peaks. Crystallinity may be measured relative to a quartz standard by comparing the peak areas for the reflection from the 200 plane (d=4.57±0.04 Å) and the 221 plane (d=3.91±0.02) for the zeolitic material of the invention with the peak area for the reflection from the 110 plane (d=2.46±0.02) of the quartz. The ratio of the combined peak areas of the 220 and 221 reflections of the zeolitic material to the peak area of the 110 reflection of quartz is a measure of the crystallinity of the sample. To provide a comparison between different samples and to eliminate cation effects the peak area determination is preferably carried out on the same cation form of the zeolite, and in the Examples given herein the potassium form was chosen.

The exchangeable cation M in general formula I is very preferably potassium, but it is possible for a part of M to be replaced by other cations such as alkali and alkaline earth metals for example sodium, rubidinium or caesium. The ratio $M_{2/n}O:Al_2O_3$ is preferably from about 0.95 to about 1.15, and generally above 1.

In general formula I×(the mole ratio $SiO_2:Al_2O_3$) is more preferably from about 6 to about 7 and most preferably from about 6.0 to about 6.5.

The aluminosilicate forms of the invention may be hydrated, typically with from 0 to about 9 moles of water per mole of $Al_2O_3$. When used as a catalyst base, as described hereinafter, the zeolite of the invention is preferably first calcined to remove water. In normal preparation from aqueous gels a hydrated form is first prepared and this may be dehydrated by heating.

Scanning electron micrographs (SEM) of the materials of the invention show these to have very distinct crystal morphology. As described in more detail hereinafter, preferred materials of the invention appear as distinct cylinders in scanning electron micrographs. The terms "cylinder" and "cylindrical" are used herein to describe particles having substantially the shape of a cylinder as defined in solid geometry—that is, a solid bounded by a surface generated by a line moving parallel to a fixed line so as to cut a fixed plane curve and by two parallel planes (bases) which cut the surface. The use of these terms is not intended to exclude particles, having generally cylindrical forms but having minor surface irregularities or displaying typical crystallographic faults of dislocations. The cylindrical particles of the invention are preferably substantially in the form of circular cylinders (circular cross-section) and most preferably substantially in the form of right circular cylinders (wherein the bases are normal to the cylinder axis). Particularly preferred cylindrical particles are those having an aspect ratio (the length of the cylinder surface to the diameter of the cylinder) of at least 0.5. Particles having a lower aspect ratio are also described as discs where they have substantially flat basal planes. Cylindrical particles including discs, have been shown to have excellent properties of extending catalyst life when used as catalyst bases for aromatization catalysts. This is in contrast to other morphologies, and in particular particles with cylindrical morphology have been shown better than particles with a clam-like shape. The term "clam" is used to describe particles having two generally convex faces joined to give the appearance of a clam shell. The aluminosilicates of the invention are preferably characterized by at least about 50%, more preferably about 70% and most preferably about 85%, of the crystallites being cylinders. The aspect ratio of the cylindrical crystallites is preferably from about 0.5 to about 1.5.

A further particularly surprising feature of the invention is that large crystallites wherein the mean diameter of the cylinders is at least about 0.1 micron may be prepared. The cylindrical particles preferably have a mean diameter of at least about 0.5 micron and this invention provides zeolites comprising these large cylindrical crystallites. The crystallites are more preferably from about 0.5 to about 4 u, and most preferably from about 1.0 to about 3.0 u. It is a further feature of the invention that there is a relatively narrow particle size distribution, and preferably substantially all the cylindrical particles of zeolite fall within the range of from 0.5 to 4 u. Transmission electron diffraction indicate these are single crystals rather than agglomerates. It is a further surprising feature of the invention that the zeolite with cylindrical morphology may be prepared by controlling the composition of the reaction mixture within certain limits, depending upon the aspect ratio required, and that by operating within these limits it is possible to obtain relatively large cylindrical particles in a narrow size distribution. Thus, in another aspect the invention also provides a process for the preparation of aluminosilicates of the invention comprising cylindrical crystallites with an aspect ratio of at least 0.5, in which an alkaline reaction mixture comprising water, a source of silicon and a source of aluminium with a composition falling within the following molar ratios (expressed as oxides):

$M_2O/SiO_2$—0.22–0.36
$H_2O/M_2O$—25–90
$SiO_2/Al_2O_3$—6–15

(wherein M is a cation of valence n, and preferably potassium or a mixture of $K+M'$ in which $M'$ is an alkali metal or alkaline earth metal such as sodium, calcium, barium, or rubidium, provided that $K_2O/(M'_2O+K_2O)$ is at least 0.7) is heated to a temperature of from at least 75° C. and preferably from about 100° C. to about 250° C., more preferably from about 120° C. to about 225° C., to form the desired cylindrical aluminosilicate.

The ratio of $H_2O/(K_2O+M'_2O+SiO_2+Al_2O_3)$ is preferably greater than 6 and most preferably greater than 8.

There are four principle components to the reaction mixture or synthesis gel and thus generally:
aluminium
silicon
potassium (optionally with up to 30 mole% replaced by alkali or alkaline earth metal)
water and the relative proportions of these four components and the chosen reaction conditions are important if the desired cylindrical aluminosilicates of the invention with an aspect ratio of at least 0.5 are to be obtained. The proportions of the four components can be shown graphically in a series of four triangular graphs each showing the percentage composition of three components of the reaction with the content the fourth component being excluded from each graph. As described in more detail hereinafter FIGS. 1 to 4 shows such plots for preferred reaction mixtures giving aluminosilicates of the invention with an aspect of at least 0.5 and, by way of comparison, for reaction mixtures giving conventional Zeolite L and other zeolite and non-zeolite products. These graphs show the composition of reaction mixtures in which M is potassium alone, but it is to be understood that as described hereinbefore up to 30 mole % of potassium may be replaced by another alkali or alkaline earth metal and the graphs are to be interpreted with that in mind.

The four graphs together may be considered as the four faces of a three-dimensional graph in the form of a regular tetrahedron, and the points and areas marked thereon represent the projection on those faces of points and volumes within the three-dimensional graph. Thus, while a point may lie within the area designated as constituting the invention in one graph, unless it lies within the area of the invention on all four graphs it does not lie within the volume defined within the three-dimensional graph as being a preferred reaction mixture of the invention.

FIG. 1 is a triangular graph of the content of the reaction mixture (in weight percentage of oxides excluding alumina) showing the relative properties of water, silicon and potassium. To obtain the preferred aluminosilicates of the invention the reaction mixture should desirably lie within the area marked $I_A$ in the graph, preferably within the area marked $II_A$ in the graph and most preferably within the area marked $III_A$ in the graph.

Figure 2:
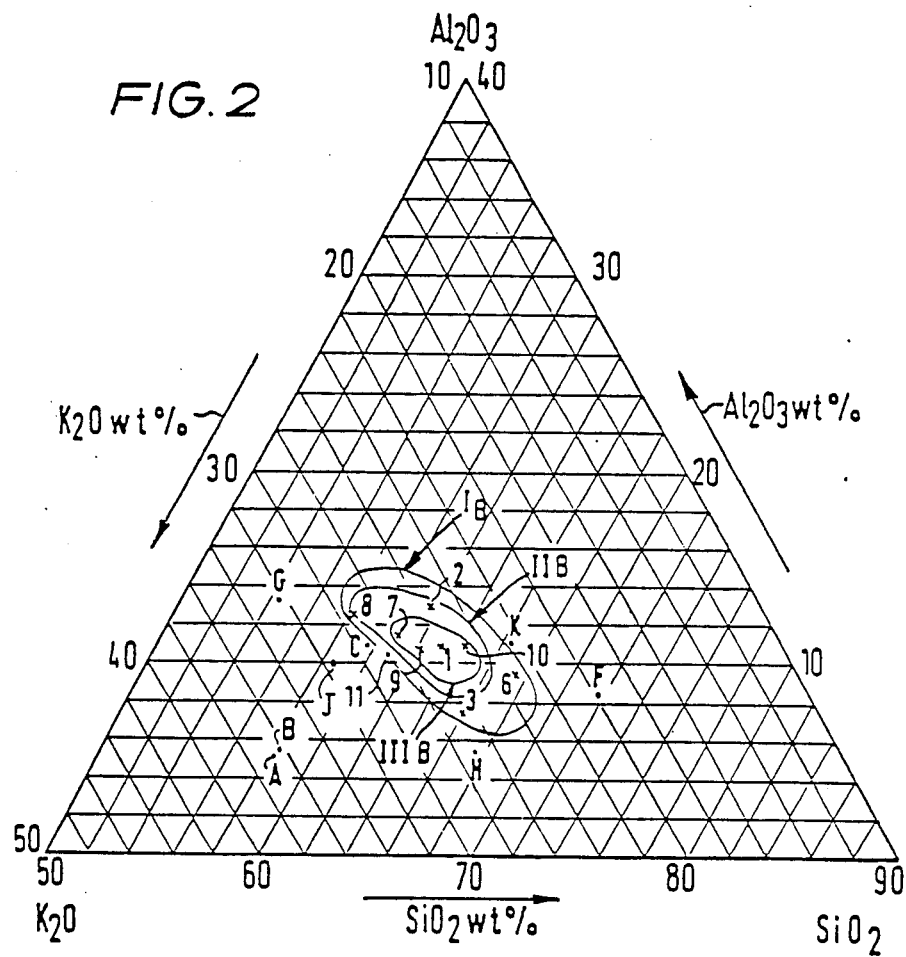

FIG. 2 is a triangular graph of the content of the reaction mixture (in weight percent of oxides excluding water) showing the relative properties of aluminium, silicon and potassium. To obtain the preferred aluminosilicates of the invention the reaction mixture should desirably lie within the area marked $I_B$ in the graph, preferably within the area $II_B$ in the graph and most preferably within the area marked $III_B$ in the graph.

Figure 3:
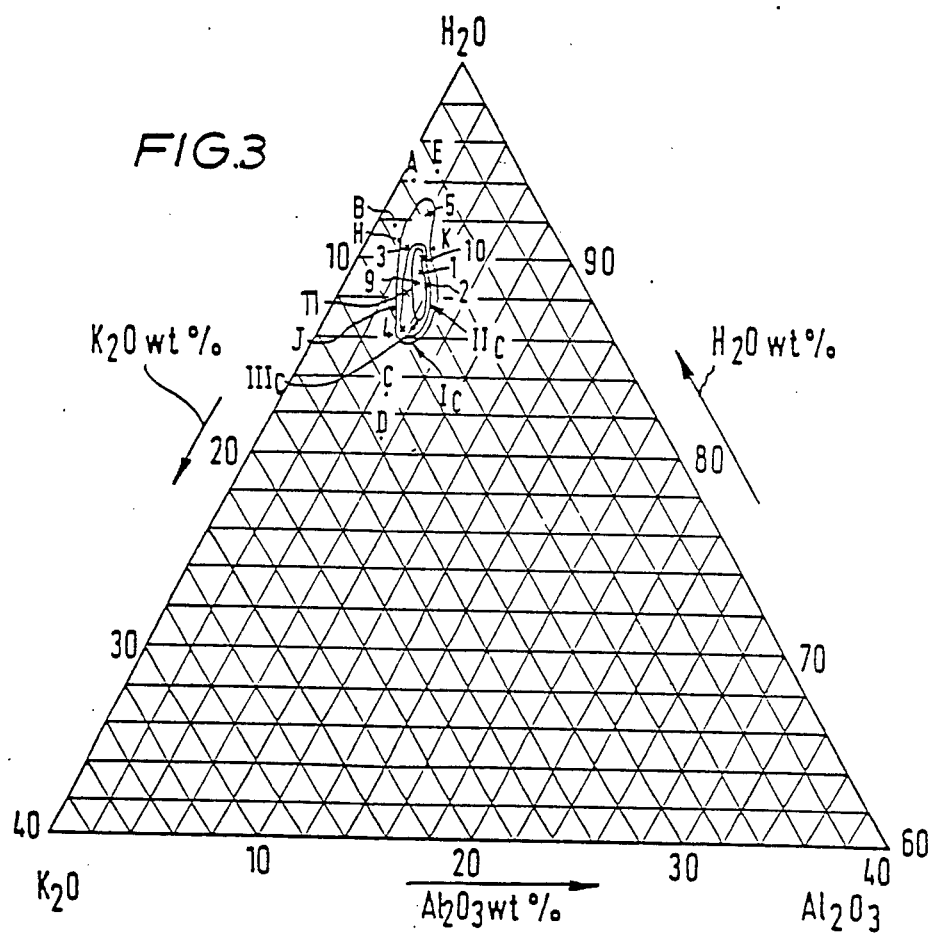

FIG. 3 is a triangular graph of the content of the reaction mixture (in weight percent of oxides excluding silica) showing the relative properties of aluminium, water and potassium. To obtain the preferred aluminosilicates of the invention the reaction mixture should desirably lie within the area marked $I_C$ in the graph, preferably within the area $II_C$ in the graph and most preferably within the area marked $III_C$ in the graph.

Figure 4:
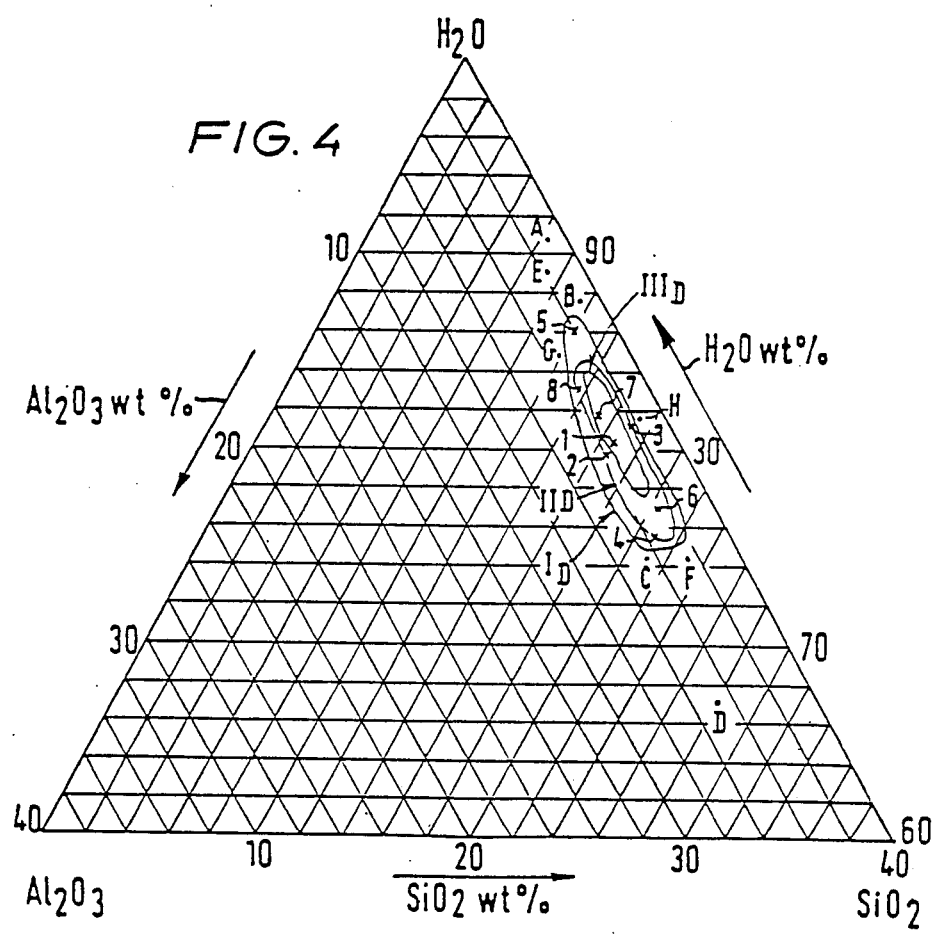

FIG. 4 is a triangular graph of the content of the reaction mixture (in weight percent of oxides excluding potassium oxide) showing the relative properties of aluminium, silicon and water. To obtain the preferred aluminosilicates of the invention the reaction mixture should desirably lie within the area marked $I_D$ in the graph, preferably within the area $II_D$ in the graph and most preferably within the area marked $III_D$ in the graph.

Very preferably the reaction mixture falls within the areas marked $III_A$, $III_B$, $III_C$ and $III_D$ in the graphs of FIGS. 1, 2, 3 and 4, respectively. Such a reaction mixture results in the highest proportion of well-defined crystals particularly when the reaction mixture is heated to the preferred temperature range of about 120° C. to about 225° C., and most preferably to a temperature of about 150° C.

Zeolite W tends to be formed in some extremes of gel composition. It is advantageous for the zeolite W content of the product to be minimized. The zeolite W content of the product can be monitored by its X-ray diffraction pattern. A characteristic prominant line in the zeolite W XRD pattern is at $2\theta=12.6°$ (d=7.09 Å), while a prominant line in the zeolite L XRD pattern is at $2\theta=22.7°$ (d=3.91 Å). The relative peak intensities of these peaks can be compared to determine the relative proportions of the two zeolite types, since these peaks are not obscured in mixtures of the two zeolites. It is a preferred feature that zeolite of the invention has an XRD pattern in which the peak height ratio (d=7.09 Å)/(d=3.91 Å) is not greater than 0.2. Very preferably the product is substantially free of zeolite W as evidenced by an absence of the XRD pattern of a line at a d spacing of 7.09 Å. To achieve this low level of zeolite W contamination the reaction mixture preferably comprises the reactants in the following molar ratios:

$$M_{2/n}O/SiO_2 = >0.25$$

$$H_2O/M_{2/n}O = <65$$

$$SiO_2/Al_2O_3 = 7.5{-}10.5$$

Products with particularly high peak intensities, measured as defined hereinbefore, have been obtained by employing a reaction mixture comprising the reactants in the following molar ratios:

$$M_{2/n}O/SiO_2 = 0.21{-}0.36$$

$$H_2O/M_{2/n}O = 28{-}80$$

$$SiO_2/Al_2O_3 = 8.5{-}10.7$$

Furthermore, the formation of crystallites with cylindrical morphology with an aspect ratio in excess of 0.5 is found to be favoured by employing a reaction mixture comprising the reactants in the following molar ratios:

$$M_{2/n}O/SiO_2 = >0.2$$

$$H_2O/M_{2/n}O = >40$$

$$SiO_2/Al_2O_3 = <22$$

In particular, an optimum composition for a process in which the reaction mixture is heated to from about 120° C. to about 225° C. has been found to be substantially in the following mole ratios:

$$2.62 K_2O{:}Al_2O_3{:}10 SiO_2{:}160 H_2O$$

and particularly good results have been obtained by heating to about 150° C. Investigation of individual variations in the components at a crystallizaton temperature of 150° C. has shown that good yields of cylindrical aluminosilicate are obtained if the water content in the optimum composition is reduced to 120 moles in the above ratio, but that further reduction in the water content still results in the formation of a good yield of Zeolite L but increasingly in the form of clam-shaped particles. In particular, at 80 moles water a high yield of clams is obtained. Thus, at the mole ratio of $H_2O/K_2O + Na_2O + Al_2O_3 + SiO_2$ less than 6 specified in GB 1 202 511 the aluminosilicates of the invention are not obtained. If the water content in the optimum ratio is increased the aluminosilicate of the invention is still obtained at 240 moles water, but at 320 moles water a significant amount of contaminating Zeolite W phase is obtained.

Similarly it is possible to obtain the aluminosilicate of the invention if the silica content in the optimum composition is varied between about 8 and about 12 moles, but at higher levels of silica there is an increasing proportion of amorphous material and at lower levels of silica Zeolite W again is produced in larger amounts.

The reaction mixture is particularly sensitive to the content of $K_2O$ (or of $M_2O$ as defined hereinbefore) and variations in the $K_2O$ content in the optimum composition beyond the range of about 0.24 to about 0.30 moles gave at higher levels of $K_2O$ an increasing proportion of clam-shaped Zeolite L particles and at lower levels of $K_2O$ a less crystalline product.

The variation of alumina content from that specified in the optimum composition set out above shows that variation of alumina from about 0.6 to about 1.3 moles was possible with the aluminosilicate of the invention still being a product. Low levels of alumina of the order of 0.5 moles resulted in an amorphous product.

Thus, the preferred aluminosilicates of the invention may be obtained within the following preferred ranges:

$K_2O/SiO_2$—0.24–0.30

$H_2O/K_2O$—35–65

$SiO_2/Al_2O_3$—8–12

In addition to varying the proportions of the reactants in the reaction mixture it is possible to vary the reaction conditions and in particular the crystallization temperature. By using different temperatures it is possible to deviate further from the optimum composition defined above for a crystallization temperature of 150° C. and yet still obtain the desired product. In general, within the broad reactant ratios defined for the process of the invention a higher crystallization temperature enables the silicon content to be lowered and/or the water content to be lowered and/or the potassium content (and thus the alkalinity) to be raised. By contrast operating at lower temperatures tends to decrease the nucleation rate which can be countered by lowering the alkalinity and/or by increasing the water content and/or by introducing seeds of preformed zeolite L. When operating in larger scale syntheses it has been found advantageous to minimise the temperature difference at any time within the crystallization gel, preferably to not more than 15° C., more preferably not more than 10° C. This may be done by a slow heating of the crystallization vessel or by limiting the maximum wall temperature of the heat-up.

A disc-shaped material of the invention, having an aspect ratio of less than 0.5, which also shows an improvement over conventionally prepared zeolite L when used as a catalyst base in aromatization, may be prepared from somewhat different synthesis gels. An optimum synthesis gel composition for forming a disc-shaped product at a temperature of from about 120° C. to about 225° C., and particularly about 150° C., has substantially the following mole ratios:

$$16 K_2O{:}Al_2O_3{:}40 SiO_2{:}64 OH_2O$$

and similar consideration apply in varying the composition or temperature as discussed hereinbefore. Preferred ranges of the ratio of the components for the production of disc-shaped products are as follows:

$$M_{2/n}O/SiO_2 = 0.23{-}0.36$$

$$H_2O/M_{2/n}O = 30{-}80$$

$$SiO_2/Al_2O_3 = 20{-}60$$

In the synthesis of all zeolitic materials of the invention, the source of silicon for the reaction mixture is generally silica, and this is usually most conveniently in the form of a colloidal suspension of silica such as Ludox HS 40 available from E. I. Dupont de Nemours and Co. Colloidal silicon sols are preferred since they result in less contaminating phases. However other forms such as silicates may be used.

The source of aluminium may be an alumina introduced into the reaction medium as, for example, $Al_2O_3.3H_2O$, previously dissolved in alkali. However, it is also possible to introduce aluminium in the form of the metal, which is dissolved in alkali.

The aluminosilicates of the invention are preferably obtained from reaction mixtures containing potassium. This potassium is preferably introduced as potassium hydroxide. The reaction mixture may contain small quantities of other metal cations and salt forming anions as already described, but it has been found that there is an increasing tendency for other aluminosilicates to be found as the content of other ions is increased, resulting in less pure forms of the aluminosilicate of the invention. For example, sodium and rhubidium ions favour erionite formation, caesium ions favour pollucite formation. Thus it is highly preferred for potassium hydroxide to be the source of potassium and the source of alkalinity, and the purest products were obtained when other potassium salts were excluded.

The product of the processes described above is predominantly a potassium form of the aluminosilicate—that is, aluminosilicate where M in general formula I is K. By ion exchange of the product in the manner conventional to zeolite chemistry other cations such as Na or H can be introduced for M.

Within the ranges specified hereinbefore for the composition of the reaction mixture it is possible to choose ratios of oxides and alkalinity to given particular forms of the aluminosilicate product. However, although the $SiO_2/Al_2O_3$ ratio in the reaction mixture may vary over a wide range the $SiO_2/Al_2O_3$ ratio in the product preferably lies in a relatively narrow range of 5.7 to 7.4. The higher the $SiO_2/Al_2O_3$ ratio in the reaction mixture, the higher the ratio in the product. Also, decreasing alkalinity ($OH^-/SiO_2$) tends to increase the $SiO_2/Al_2O_3$ ratio in the formed product. Dilution of the reaction mixture with water and thus increasing the $H_2O/K_2O$ ratio also tends to increase the $SiO_2/Al_2O_3$ ratio in the product. Other cations such as tetramethylammonium and the presence of other potassium salts can be used to raise the $SiO_2/Al_2O_3$ ratio, but as described hereinbefore this may also result in the formation of other zeolite forms.

Particle size is also affected by the composition of the reaction mixture. Generally the particles formed are in the range of from about 0.5 to about 4.0 u, but within that range larger particle sizes are favoured by each of lower alkalinity, higher dilution and higher temperatures.

Crystallization is related to the crystallization temperature. The crystallization is preferably carried out in the region of 150° C. and at this temperature the crystallization time may be from about 24 to 96 hours, typically from 48 to 72 hours. Lower temperatures may require such longer times to achieve good yield of the desired product, whereas times of less than 24 hours are possible when higher temperatures are used. A time of 8 to 15 hours is typical for a temperature of greater than 200° C.

The crystallization is generally carried out in a sealed autoclave and thus at autogenous pressure. It is generally inconvenient, although possible to employ higher pressures. Lower pressure will require longer crystallization times.

Following the preparation as described above the aluminosilicate may be separated, washed and dried in the normal manner.

The products of the processes of the invention described hereinbefore are preferably substantially free from contaminant crystalline and amorphous materials. However, in employing these products in catalytic applications it may be desired to combine them with additional crystalline or amorphous materials and this invention extends to such combinations.

We have found that the aluminosilicates of the invention are excellent catalyst bases and may be used in a wide variety of catalytic reaction. The particular morphology of the crystals appears to result in a particular stable base for catalytically active metals with a surprising resistance to metal catalyst deactivation. In addition, the aluminosilicates of the invention have displayed low acidity which makes them especially suited to catalytic applications where a low acid site strength is advantageous such as aromatization.

The catalytically-active metal(s) may be, for example, a Group VIII metal such as platinum, tin, or germanium as described in U.S. Pat. No. 4,104,320, or a combination of platinum and rhenium as described in GB No. 2 004 764 or BE No. 888365. In the latter case the catalyst may for appropriate circumstances also incorporate halogen as described in U.S. Pat. No. 4,165,276, silver as described in U.S. Pat. No. 4,295,959 and U.S. Pat. No. 4,206,040, cadmium as described in U.S. Pat. No. 4,295,960 and U.S. Pat. No. 4,231,897 or sulphur as described in GB No. 1 600 927.

We have found a particularly advantageous catalyst composition to incorporate from about 0.1 to about 6.0 weight %, preferably from about 0.1 to about 1.5 weight % platinum or palladium, since this gives excellent results in aromatization. From about 0.4 to about 1.2 wt % platinum is particularly preferred, especially in conjuction with the potassium form of the aluminosilicate. The invention extends to catalysts comprising the zeolitic material and a catalytically-active metal.

It may also be useful to incorporate into the catalyst of the invention one or more materials substantially inert under the conditions in which the catalyst is to be employed to act as a binder. Such binders may also act to improve the resistance of the catalyst to temperature, pressure and attrition.

The aluminosilicates of the invention may be used in a process for the conversion of a hydrocarbon feed in which the feed is contacted with a catalyst as described above under appropriate conditions to bring about the desired conversion. They may for example be useful in reactions involving aromatization and/or dehydrocyclization and/or isomerization and/or dehydrogenation reaction. They are particularly useful in a process for the dehydrocyclization and/or isomerization of acyclic hydrocarbons in which the hydrocarbons are contacted at a temperature of from about 430° C. to about 550° C. with a catalyst comprising an aluminosilicate of the invention having at least 90% of the exchangeable cations M as alkali metal ions and incorporating at least one Group VIII metal having dehydrogenating activity, so as to convert at least part of the acyclic hydrocarbons into aromatic hydrocarbons.

The process is preferably otherwise carried out in the manner described in U.S. Pat. No. 4,104,320, BE No. 888365 or EP No. 40119.

It has been found that use of the aluminosilicates of the invention in this way enables greatly improved catalyst lifetimes to be achieved as compared to the lifetime obtained with a conventionally prepared zeolite.

Figure 5:
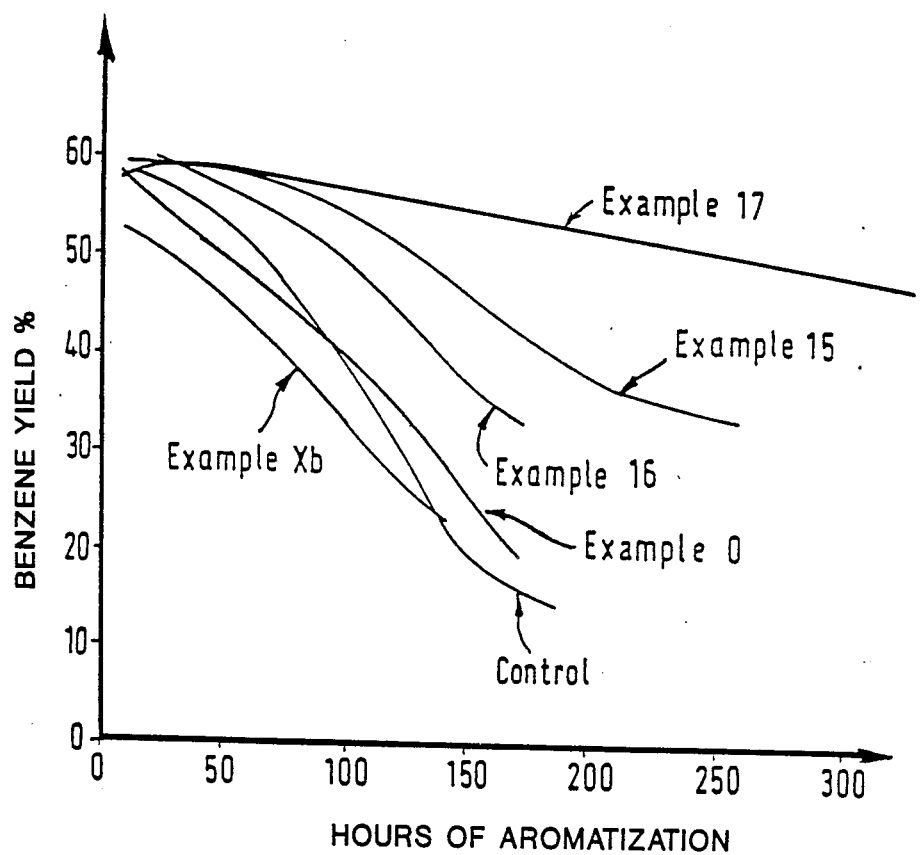
FIG. 5 is a graph showing the aromatization performance of catalysts using the zeolites of this invention and other conventional catalysts.

The invention will now be described in more detail, though only by way of illustration, in the following Examples and Evaluations, with reference to the accompanying drawings, in which:

FIGS. 1 to 4 are, as described hereinbefore, triangular graphs showing the preferred proportions of components of the synthesis gel. On these graphs the reaction mixtures used in the Examples in the production of aluminosilicates of the invention are shown as crosses identified by the number of Example, and those reaction mixtures used in the Comparative Examples are shown as solid circles identified by the letter of the Comparative Example; and FIG. 5 is a graph showing the performance of catalysts of the invention in aromatization against catalysts based on conventional zeolites.

For convenience, the aluminosilicates of the invention will be referred to as "zeolite EL" or simply "EL".

EXAMPLE 1

Preparation of Zeolite EL

A synthesis gel was prepared having the following composition expressed in moles of pure oxide:

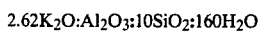

$2.62 K_2O : Al_2O_3 : 10 SiO_2 : 160 H_2O$

This gel was prepared as follows: 23.40 g of aluminium hydroxide was dissolved by boiling in an aqueous solution of 51.23 g of potassium hydroxide pellets (86% pure KOH) in 100.2 g to form solution A. After dissolution any water loss was corrected. A separate solution, solution B, was prepared by diluting a 225 g of colloidal silica (Ludox HS40) with 195.0 g of water.

Solutions A and B were mixed for two minutes to form 224 g of gel, and just before the gel became fully stiff it was transferred to Teflon-lined autoclaves, preheated to 150° C. and held at that temperature for 72 hours to bring about crystallization.

The formed Zeolite EL was highly crystalline with a typical Zeolite L X-ray diffraction (XRD) pattern. Scanning electron micrographs (SEM) show the product to be formed solely of well-defined cylindrical crystals having a particle size of 2 to 2.5 microns. The $SiO_2:Al_2O_3$ ratio in the product was 6.3. $K_2O:Al_2O_3$ was measured as 0.99.

COMPARATIVE EXAMPLE A

Repetition of U.S. Pat. No. 3,867,512. Example 9

A synthesis gel was prepared using the procedure of Example 9 of U.S. Pat. No. 3,867,512 which is judged to be the disclosure in that prior art document which provides the most relevant comparison with the invention, although presented in U.S. Pat. No. 3,867,512 as a comparative example. 2.92 g of aluminium hydroxide were dissolved in a solution of 19.52 g potassium hydroxide in 25.0 g water to form solution A. 56.5 g Ludox HS40 were dissolved in 101.0 g water to form solution B. Solutions A and B were mixed for two minutes to form synthesis gel.

Crystallization was carried out at 116° C. for 68 hours, and the product was separated as in Example 1. The gel combination was:

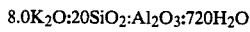

$8.0 K_2O : 20 SiO_2 : Al_2O_3 : 720 H_2O$ and thus very dilute, and more alkaline than required by the present invention. The product was Zeolite L but contained no cylindrical crystallites which are the characteristic product of the present invention.

COMPARATIVE EXAMPLE B

Repetition of Nishimura

The synthesis procedure described in Y Nishimura, Nippon Kagaku Zasshi 91, 11, 1970, pp 1046-9 was repeated to prepare a gel composition:

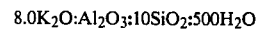

$8.0 K_2O : Al_2O_3 : 10 SiO_2 : 500 H_2O$

This was crystallized in an autoclave at 100° C. for 65 hours.

The Japan disclosure is of gels which are more dilute and of high alkalinity than required for the present invention. The product of this Comparative Example was essentially Zeolite W, not Zeolite L and there was no trace of Zeolite EL of this invention.

COMPARATIVE EXAMPLE C

Repetition of DT No. 1813099 Example 6

A synthesis gel was prepared having substantially the composition described in Example 6 of DT No. 1813099 (equivalent to GB No. 1 202 511):

$2.75 K_2O : Al_2O_3 : 8.7 SiO_2 : 100 H_2O$ 7.37 g of aluminium hydroxide were dissolved in an aqueous solution of 16.98 gms of potassium hydroxide (86% pure KOH) in 30.9 gms water to Solution A. 25.04 g of silica as Aerosil 200 were mixed with 55.4 g water for 5 minutes to form Solution B. Solutions A and B were mixed for 1 minute and the formed putty-like gel was heated in an autoclave at 140° C. for 46.5 hours.

The product was separated and dried as in Example 1. XRD and SEM showed the product to be a mixture of Zeolite W with Zeolite L. No cylindrical crystallites characteristic of the invention were observed. The procedure of DT No. 1813099 used drier gels than the present invention and somewhat higher alkalinity, so that effectively the gel alkalinity was significantly higher.

EXAMPLES 2 AND 3 AND COMPARATIVE EXAMPLE H

Variation of Aluminium Content

The general procedure of Example 1 was repeated with different amounts of aluminium present in the gel. The gels employed are detailed in Table 1 below, together with an indication of the products obtained.

Example 3 ($2.58 K_2O : 0.67 Al_2O_3 : 10 SiO_2 : 160 H_2O$) and Example 2 ($2.62 K_2O : 1.25 Al_2O_3 : 10 SiO_2 : 160 H_2O$) yielded Zeolite EL of the invention and Example 3 gave a particularly high yield (20%-measured as zeolite product as a percentage of the initial gel weight). Comparative Example H ($2.58 K_2O : 0.5 Al_2O_3 : 10 SiO_2 : 160 H_2O$) gave a largely amorphous product.

EXAMPLES 4 AND 5 AND COMPARATIVE EXAMPES D AND E

Variation of Water Content

The procedure of Example 1 was repeated for further syntheses using various amounts of water. The gel composition and results are given in Table 1 below.

Example 4 ($2.62 K_2O : Al_2O_3 : 10 SiO_2 : 120 H_2O$) gave good yields of cylindrical Zeolite EL, but as the water content is further reduced there is a tendency to form clam-shaped particles. Comparative Example D (2.62K$_2$O:Al$_2$O$_3$:10SiO$_2$:80H$_2$O) resulted in a high proportion of clam Zeolite L.

Example 5 shows that increasing the water content to 240 moles H$_2$O still resulted in Zeolite EL, but as water is increased there is an increasing product of Zeolite W. At 320 moles H$_2$O in Comparative Example E Zeolite W predominates.

EXAMPLES 6-8 AND COMPARATIVE EXAMPLES F AND G

Variation in Silicon Content

A similar investigation of the variation of silicon content of the synthesis gel of Example 1 was carried out as shown in Table 1. Increasing silicon content resulted in an increasing amount of contaiminating phases of Zeolite W and amorphous material, but Example 6 with 12 moles SiO$_2$ gave a satisfactory Zeolite EL product. Comparative Example F using 15 moles SiO$_2$ gave a largely amorphous product.

The silicon content was reduced in Example 8 to 8 moles SiO$_2$ with satifactory Zeolite EL product, but further reduction to 7 moles SiO$_2$ in Comparative Example G gave a product containing Zeolite W and Zeolite L.

EXAMPLES 9, 10 AND 11 AND COMPARATIVE EXAMPLES J AND K

Variation of Potassium Content

As shown in Table 1, the variation of the amount of potassium in the case where M=K was also investigated. Variation of potassium content from 2.41 moles K$_2$O (Example 10) to 2.75 moles K$_2$O (Example 9) gave Zeolite EL. Example 11 gave Zeolite L with a morphology intermediate the clam shape and the cylinder shape.

A low potassium content of 2.15 moles K$_2$O (Comp. Ex. K) gave a product with low crystallinity. A high potassium content of 3.4 moles K$_2$O (Comp. Ex. J) gave a clam-shaped product.

the areas of preferred gel composition marked on the Figures correspond to gels yielding zeolite EL.

Various additional tests have been carried out on substitution of potassium by other metals such as sodium. Since this introduces a further variable it is not possible to show these results in FIGS. 1 to 4.

EXAMPLES 12-14

Replacement of Potassium

Example 1 was repeated in a generally similar manner but a part of the potassium hydroxide used in preparing Solution A was replaced by sodium hydroxide. Replacement of 10, 20 and 30 mole % was effected and product were obtained and analysed by XRD and SEM. The results are set out in Table 2 below:

TABLE 2

| Example | Gel Composition (moles) | | | | | Product |
|---|---|---|---|---|---|---|
| | K$_2$O | Na$_2$O | Al$_2$O$_3$ | SiO$_2$ | H$_2$O | |
| 12 | 2.36 | 0.26 | 1 | 10 | 160 | cylindrical zeolite EL |
| 13 | 2.10 | 0.52 | 1 | 10 | 160 | cylindrical zeolite EL |
| 14 | 1.83 | 0.78 | 1 | 10 | 160 | cylindrical zeolite EL |

COMPARATIVE EXAMPLE L

Repetition of U.S. Pat. No. 3,216,789 Example 4

The procedure of Example 4 of U.S. Pat. No. 3,216,789 was repeated to prepare a synthesis gel of molar composition (based on actual purities of reactants):

(2.7K$_2$O+0.7Na$_2$O):Al$_2$O$_3$:10SiO$_2$:135H$_2$O

This was then crystallized at 150° C. for 45 hours and worked up as described in U.S. Pat. No. 3,216,789. The product was a crystalline zeolite L but the crystallites were clam-shaped and there was no trace of cylindrical Zeolite EL of the invention. This result is consistent with the trend noted in increasing alkalinity from Example 9 to Comparative Example J.

TABLE 1

| | GEL COMPOSITION | | | | | | | | |
|---|---|---|---|---|---|---|---|---|---|
| | (moles) | | | | (wt %) | | | | |
| EXAMPLE | K$_2$O | Al$_2$O$_3$ | SiO$_2$ | H$_2$O | K$_2$O | Al$_2$O$_3$ | SiO$_2$ | H$_2$O | PRODUCT* |
| 1 | 2.62 | 1 | 10 | 160 | 6.4 | 2.7 | 15.7 | 74.6 | cylindrical zeolite EL |
| 2 | 2.62 | 1.25 | 10 | 160 | 6.4 | 3.4 | 15.6 | 74.6 | zeolite L |
| 3 | 2.58 | 0.67 | 10 | 160 | 6.4 | 1.8 | 15.8 | 76.0 | cylindrical zeolite EL + |
| H | 2.58 | 0.50 | 10 | 160 | 6.4 | 1.4 | 15.9 | 76.3 | amorphous |
| 4 | 2.62 | 1 | 10 | 120 | 7.9 | 3.3 | 19.3 | 69.5 | cylindrical zeolite EL |
| 5 | 2.62 | 1 | 10 | 240 | 4.7 | 1.9 | 11.4 | 82.0 | cylindrical zeolite EL + (W) |
| D | 2.62 | 1 | 10 | 80 | 10.3 | 4.3 | 25.1 | 60.3 | clam-shaped zeolite L |
| E | 2.62 | 1 | 10 | 360 | 3.7 | 1.5 | 8.9 | 85.9 | zeolite W + (zeolite L) |
| 6 | 2.62 | 1 | 12 | 160 | 6.2 | 2.6 | 18.2 | 72.9 | zeolite EL + (W + amorphous) |
| 7 | 2.62 | 1 | 9 | 160 | 6.5 | 2.7 | 14.3 | 76.4 | cylindrical zeolite EL |
| 8 | 2.58 | 1 | 8 | 160 | 6.5 | 2.8 | 13.0 | 77.7 | cylindrical zeolite EL (+W) |
| F | 2.62 | 1 | 15 | 160 | 6.0 | 2.5 | 21.8 | 69.8 | amorphous |
| G | 2.62 | 1 | 7 | 160 | 6.8 | 2.8 | 11.5 | 78.9 | zeolite W + (zeolite L) |
| 9 | 2.75 | 1 | 10 | 160 | 6.7 | 2.7 | 15.6 | 75.0 | cylindrical zeolite EL |
| 10 | 2.41 | 1 | 10 | 160 | 5.9 | 2.7 | 15.8 | 75.6 | cylindrical zeolite EL |
| 11 | 3.01 | 1 | 10 | 160 | 7.3 | 2.6 | 15.5 | 74.5 | clam/cylinder zeolite EL |
| K | 2.15 | 1 | 10 | 160 | 5.3 | 2.7 | 15.9 | 76.1 | low crystallinity product |
| J | 3.4 | 1 | 10 | 160 | 8.2 | 2.6 | 15.4 | 73.8 | clam-shaped zeolite L |

"+" indicates that small amounts of other phases were present. Where other phases were identified these are shown in parenthesis.

FIGS. 1 to 4 plot the relative proportions of the components of the gel composition and the preferred proportions for these components in the process of the invention. The Examples of the invention are marked as numbered crosses and the Comparative Examples are shown as lettered dots. This clearly demonstrates that

COMPARATIVE EXAMPLE M

Repetition of Tsitsishvilli

The synthesis procedure described in Tsitsishvilli et al, Doklady Akademii Nauk SSSR, Vol 243, No 2, pp 438–440 (1973) was repeated to prepare a gel with a molar composition:

$$5.99K_2O:12.00Na_2O:Al_2O_3:25SiO_2:360H_2O$$

and containing tributylamine at a rate of 37 ml tributylamine in 132 g of gel. This was crystallized at 100° C. for 45 hours.

This synthesis, which differs from the invention in using high alkalinity, high sodium content and an organic component, gave a product that was largely Zeolite W with a second unidentified phase. No Zeolite EL was identified in the product.

EXAMPLE 15

Zeolite EL Preparation Using Aluminium as Metal

A synthesis gel of 133 g was prepared having a composition (measured as moles of pure oxide per mole of aluminium measured as $Al_2O_3$) 2.60 moles $K_2O$, 10 moles $SiO_2$ and 160 moles water. The following method was employed:

Aluminium pellets were dissolved in an aqueous solution of potassium hydroxide (86% pure) by heating. After complete dissolution extra water was added to correct for weight losses. Finally the silica source, a diluted Ludox HS 40 solution, was added. The mixture containing all components was mixed for 4 minutes in a high sheer mixer. The resulting aluminosilicate gel was charged to a clean Teflon-lined autoclave (within a few minutes a very viscous gel is obtained). The filled autoclave was put in an already heated oven (150° C.) and maintained at that temperature for 48 hours to allow zeolite crystallization.

The solid product was separated by centrifuging, washed with cold water (4 times) and dried at 150° C. for 4 hours.

The formed Zeolite EL was in the form of large (1.5–2.5 u) crystals with a cylindrical shape. The $SiO_2/Al_2O_3$ ratio in the product was 6.3.

EXAMPLE 15 AND COMPARATIVE EXAMPLES O TO W

The procedure of Example 15 was repeated with different synthesis gels to form various Zeolite L samples. The synthesis gels and the products obatined are summarized in Table 3 below. Example 16 formed a disc-shaped zeolite EL product with good crystallinity. In the Comparative Examples the Zeolite EL product of the invention was not obtained.

TABLE 3

| EXAMPLE | GEL Wt (g) | GEL COMPOSITION (moles) | | | | PRODUCT | | | |
| | | $K_2O$ | $SiO_2$ | $Al_2O_3$ | $H_2O$ | Zeolite | Shape | Size (u) | $SiO_2/Al_2O_3$ |
|---|---|---|---|---|---|---|---|---|---|
| 16 | 116 | 14.1 | 40 | 1 | 640 | EL | Disc | 0.5–1 | 7.4 |
| O | 270 | 3.5 | 10 | 1 | 160 | L | Clam | 1.5–2.6 | 5.6 |
| P | 230 | 3.5 | 20 | 1 | 640 | Amorphous | — | — | |
| Q | 140 | 3.5 | 20 | 1 | 160 | Amorphous | — | — | |
| R | 114(a) | 3.5 | 10 | 1 | 160 | L | Sphere | 0.3–0.5 | 5.6 |
| S | 134(b) | 3.5 | 10 | 1 | 160 | L | Clam | 1.5–2.5 | 6.1 |
| T | 134(c) | 3.5 | 10 | 1 | 160 | L | Clam | 1.5–2.5 | 5.8 |
| U | 138 | 4.4 | 10 | 1 | 160 | L | Sphere | 0.3–0.5 | 5.0 |
| V | 135 | 3.5 | 10 | 1 | 160 | L | Clam | 1–2.5 | 5.4 |
| W | 83 | 3.5 | 10 | 1 | 84 | L | Sphere | 0.1–0.2 | 5.4 |

(a)silicon source = hydrated silicic acid $SiO_2.nH_2O$
(b)aluminum source = 50% Al 50% $Al_2O_3.3H_2O$
(c)aluminum source = 25% Al 75% $Al_2O_3.3H_2O$

COMPARATIVE EXAMPLES X

Effect of Anions

Example 15 was repeated except that an additional mole of potassium (measured as moles $K_2O$/mole $Al_2O_3$) was introduced as a potassium salt. This gave the gel the following composition (in terms of moles of oxides):

$$3.5K_2O:Al_2O_3:10SiO_2:160H_2O$$

The products of the crystallization showed mixed crystallite types which indicated that mixtures of zeolite types were formed. Zeolite W was identified by its X-ray diffraction pattern. The additives also increased the $SiO_2/Al_2O_3$ ratio in the product. The results are given in Table 4 which follows:

TABLE 4

| Comp Ex | Additive | Product | | | |
| | | Zeolite type | Shape | Size (u) | $SiO_2/Al_2O_3$ |
|---|---|---|---|---|---|
| Xa | KBr | L | clam & disc | 2.5–3 | 6.8 |
| Xb | KCL | L and W | clam | 3–4 | 7.2 |
| Xc | $K_2CO_3$ | L and W | clam & irregular | 2–3 | 6.5 |
| Xd | $K_2SO_4$ | L and W | disc & cylinder | 2–2.5 | 6.8 |
| Xe | K toluene sulphonate | L and W | irregular | 0.5 | 6.9 |

COMPARATIVE EXAMPLES Y

Repeat of GB No. 1 393 365

Example 10 of GB No. 1 393 365 describes a synthesis mixture with the composition:

$$2.7M_2O:Al_2O_3:8.75SiO_2:83.7H_2O$$

wherein $K_2O/M_2O$ (i.e. $K_2O+Na_2O$)=0.8 for the preparation of zeolite AG-1. GB No. 1 393 365 specifies a water glass starting material for this synthesis with the composition:

$$Na_2O:4.0SiO_2:42.6H_2O.$$

However, the use of such a silicon source makes it impossible to comply with the other requirement of GB No. 1 393 365 that the water glass should be the only or major source of silicon.

A synthesis mixture of the specified composition was prepared using potassium aluminate and Ludox Hs-40 as the raw materials. A similar synthesis (not described in GB No. 1 393 365) was also performed using a mixture containing no sodium. The results are given in Table 5 below. The products had poor crystallinity, and showed clam morphology.

TABLE 5

| Gel composition mole/mole Al$_2$O$_3$ | | | | Crystallization | | Product characteristics | | |
|---|---|---|---|---|---|---|---|---|
| Na$_2$O | K$_2$O | SiO$_2$ | H$_2$O | Temp °C. | time hrs | zeolite | shape | size (um) |
| — | 2.70 | 8.75 | 83.7 | 135 | 25 | L | clam | 0.5–1 |
| 0.54 | 2.16 | 8.75 | 83.7 | 135 | 25 | L | clam | 0.5–1 |

EXAMPLE 17

Scaled-Up Synthesis

The synthesis of Example 1 was repeated in a 2 liter autoclave with a diameter of 10.2 cms using amounts of reactants increased to give a total synthesis gel weight of 1709 grams. A heating-up period of 9 hours was employed to bring the gel to the crystallization temperature of 150° C. so that a maximum temperature difference of 10° C. was obtained in the gel. 260 grams of a highly crystalline zeolite EL product was obtained, with the crystals having a particle size of 1 to 1.5 u and substantially all of the particles having a cylindrical morphology.

X-Ray Diffraction

X-ray diffraction patterns were obtained for the product of Example 17 and Comparative Example 0, and these were compared with the patterns for EC-19, a zeolite L sample obtained from Union Carbide Corporation, and the patterns for quartz, a quartz standard called Arkansas Stone obtained from Deane Smith at the University of Pennsylvania (provided with all Phillips Instruments).

The samples for the X-ray diffraction measurements were prepared by two techniques, to give a hydrated and a dried sample.

Hydrated Sample Preparation

The sample as synthesized was loaded into a diffractometer cell without first washing. It was then hydrated by being placed for at least 16 hours in a closed vessel over saturated calcium chloride. The cell was taken from the vessel and immediately placed in the diffractometer.

Dry Sample Preparation

The sample after synthesis was washed 5–6 times with cold demiwater and the washings decanted by centrifuging. The sample was dried for 16 hours at 150° C. in air, and then homogenized by hand using a mortar and pestle, and loaded into the diffractometer cell.

Diffractometer

The XRD measurements were taken on a Phillips APD 3600 diffractometer using CuK$_\alpha$ radiation operating as follows:
X-ray tube energy: 40 mA, 45 kV
Measuring time: 0.6 sec
Scan speed: 1° 2θ/min
Scanning range: 4°–100°
Step width: 0.01°

The diffractometer incorporates a theta compensating slit and is integral with a Data General Nova 4X computer using Phillips Software to process the data.

Procedure

The XRD patterns were measured in the following sequence:
Quartz
Hydrated samples
Quartz
Dry samples
Quartz The peak heights and peak areas for quartz used in the following calculations were the average of the 3 quartz samples. The XRD patterns for d values above 2 Å are given in Tables 6 and 7.

In addition, the peak heights of the eight peaks identified in the table were summed and divided by the sum of the peak height for the peaks in the quartz pattern at d values of:
4.26±0.04
3.35±0.04
2.46±0.02

The ratio gives a measure of the relative peak height of the samples. It will be noted that the peak heights of the Example 17 product are greater than the peak heights of EC-19 or the Comparative Example O product.

Crystallinity

The XRD data was analysed to determine the ratio of the peak areas for the reflection from the plane 220 (d=4.57±0.04 Å) and 221 plane (d=3.91±0.02 Å) of the zeolite to the peak area for the reflection from the 110 plane (d=2.46±0.02 Å) of the quartz. The peaks were chosen as being in areas where there was no overlap with other peaks and being relatively insensitive to hydration effects.

For each peak the integrated area was determined and expressed as a percentage of the quartz peak. The sum of these percentages for the two peaks are given in Tables 6 and 7. A straight line background was calculated in determining these peak areas by a least-squares fit of linear equation through portions of the scan on either side of the peak in question. The area A then calculated as:

$$A = \sum_{i=T_1}^{T_2} (I_i - B_i)$$

where $I_i$ the measured intensity and $B_i$ the calculated background for each point i between $T_1$ and $T_2$ which are the initial and final 2θ integration values.

The results show the product of Example 17 to have good crystallinity.

XRD Patterns

It is noted that the dry and hydrated samples of the product of Example 17 showed an absence of reflections at d spacings of 6.28±0.05 Å.

Evaluation: Aromatization

The performance of certain of the Zeolite EL samples of the Examples as a catalyst base in aromatization was compared to products of the Comparative Examples, and a zeolite L, designated EC19, obtained from Union Carbide Corporation, referred to a "Control". In each case a catalyst was prepared by impregnating the base with 0.6 wt% platinum.

The zeolite sample under test (typically about 25 g) was slurried in 700 ml of distilled water in a 5 liter flask. The appropriate amount of tetraammino-platinum dichloride to give impregnation at a rate of 0.6 wt% platinum was dissolved in 300 ml of distilled water. The platinum salt solution was then added to the sample slurry over an 6 hour period. The mixture was stirred for 24 hours after platinum salt addition, then the impregnated sample was dried at 110° C.

The sample was then pelletized, crushed to 14-20 mesh (US sieve size) and loaded into a vertical tubular reactor and air (substantially water-free) was passed over the catalyst at a rate of 25 ml/min of air per gram of sample. The catalyst was heated to 480° C. in four hours and held at 480° C. for three hours. The sample was then reduced by passing hydrogen over it at 207 kPa and a rate of 75 ml/min per gram of sample, while the catalyst was heated to 527° C. in 3 hours, held at 527° C. for ten minutes and then cooled to the desired reaction temperature.

The aromatization test was carried out at a temperature of 510° C. and 690 KPa (100 psig) pressure with a $C_6$ mixed feed comprising:

| Component | wt % |
|---|---|
| iso-$C_6$ (3-methyl-pentane) | 30 |
| n-$C_6$ | 60 |
| methyl cyclopentane | 10 | at a space velocity of 2.5 w/w hr$^{-1}$ and in the presence of hydrogen, the $H_2$:hydrocarbon ratio being 6.

The results are shown graphically in FIG. 5, which shows the benzene yield (weight %) as a function of time. The catalyst using the cylindrical aluminosilicate of Example 15 as its catalyst base show a remarkable improved activity life time over extended periods of time, much greater than that achieved with catalysts using the clam-shaped zeolite L of Comparative Examples Xb and O or using the conventional zeolite L of the Control. The disc-shaped aluminosilicate of the invention also shows a significant advantage over the Control.

It is a further feature of the aluminosilicate of the invention that in the aromatization evaluation described herein, a catalyst comprising 0.6 wt% platinum of the aluminosilicate has a benzene yield of 45 wt% after at least 150 hours, and preferably after 200 hours.

In a repeat of this test the product of Example 17 gave benzene yields in excess of 40% for a period of 430 hours.

TABLE 6

XRD patterns of hydrated samples

| EC-19 | | Comparative Example O | | Example 17 | |
|---|---|---|---|---|---|
| d(Å) | Relative Intensity | d(Å) | Relative Intensity | d(Å) | Relative Intensity |
| 16.0 | 65 | 15.9 | 58 | 15.7 | 61 |
| 7.95 | 4 | 7.93 | 4 | 7.96 | 4 |
| 7.52 | 21 | 7.52 | 21 | 7.51 | 18 |
| 6.02 | 33 | 6.01 | 28 | 6.01 | 29 |
| 5.82 | 15 | 5.82 | 12 | 5.81 | 13 |
| *4.59 | 61 | *4.60 | 52 | *4.59 | 53 |
| 4.42 | 22 | 4.42 | 18 | 4.41 | 19 |
| 4.34 | 20 | 4.34 | 13 | 4.33 | 18 |
| *3.92 | 87 | *3.92 | 91 | *3.92 | 75 |
| 3.81 | 7 | 3.81 | 9 | 3.81 | 8 |
| *3.66 | 44 | *3.66 | 47 | *3.66 | 44 |
| *3.48 | 63 | *3.48 | 71 | *3.48 | 66 |
| 3.40 | 4 | 3.40 | 5 | 3.40 | 6 |
| *3.29 | 44 | *3.29 | 41 | *3.28 | 43 |
| *3.19 | 100 | *3.19 | 97 | *3.18 | 100 |
| *3.07 | 74 | *3.07 | 78 | *3.07 | 73 |
| 3.01 | 12 | 3.01 | 12 | 3.01 | 11 |
| *2.91 | 89 | *2.91 | 100 | *2.91 | 85 |
| 2.84 | 4 | 2.86 | 7 | 2.86 | 6 |
| 2.80 | 12 | 2.84 | 8 | 2.84 | 8 |
| 2.73 | 2 | 2.79 | 11 | 2.79 | 13 |
| 2.68 | 24 | 2.68 | 23 | 2.72 | 3 |
| 2.66 | 60 | 2.66 | 57 | 2.67 | 20 |
| 2.62 | 5 | 2.62 | 31 | 2.65 | 47 |
| 2.51 | 16 | 2.55 | 3 | 2.62 | 29 |
| 2.48 | 20 | 2.51 | 19 | 2.55 | 5 |
| 2.43 | 20 | 2.47 | 19 | 2.50 | 14 |
| 2.38 | 3 | 2.43 | 19 | 2.47 | 21 |
| 2.35 | 3 | 2.42 | 14 | 2.43 | 16 |
| 2.30 | 10 | 2.38 | 4 | 2.41 | 12 |
| 2.28 | 12 | 2.30 | 10 | 2.37 | 2 |
| 2.20 | 38 | 2.28 | 12 | 2.35 | 2 |
| 2.12 | 2 | 2.20 | 43 | 2.30 | 9 |
| 2.04 | 10 | 2.15 | 3 | 2.27 | 11 |
| 2.01 | 4 | 2.12 | 2 | 2.20 | 32 |
| | | 2.04 | 8 | 2.18 | 3 |
| | | | | 2.12 | 3 |
| | | | | 2.04 | 8 |
| | | | | 2.01 | 4 |

$$\frac{\text{Sum peak heights}}{\text{Quartz peak heights}}$$

| 0.35 | 0.32 | 0.47 |

$$100 \times \frac{\text{Zeolite 220 + 221 peak areas}}{\text{Quartz 110 peak area}}$$

| 157 | 146 | 163 |

TABLE 7

XRD patterns of dried samples

| EC-19 | | Comparative Example O | | Example 17 | |
|---|---|---|---|---|---|
| d(Å) | Relative Intensity | d(Å) | Relative Intensity | d(Å) | Relative Intensity |
| 15.7 | 63 | 15.9 | 66 | 15.8 | 81 |
| 7.90 | 4 | 9.21 | 2 | 9.15 | 2 |
| 7.49 | 19 | 8.00 | 4 | 7.93 | 6 |
| 5.99 | 34 | 7.54 | 24 | 7.51 | 21 |
| 5.80 | 16 | 6.02 | 28 | 6.00 | 31 |
| *4.58 | 59 | 5.84 | 13 | 5.81 | 13 |
| 4.41 | 22 | *4.60 | 63 | *4.59 | 56 |
| 4.33 | 18 | 4.42 | 19 | 4.41 | 19 |
| *3.91 | 86 | 4.34 | 13 | 4.33 | 18 |
| 3.80 | 8 | *3.93 | 95 | *3.92 | 83 |
| *3.65 | 43 | 3.81 | 9 | 3.81 | 7 |
| *3.47 | 59 | *3.66 | 46 | *3.66 | 48 |
| 3.39 | 5 | *3.49 | 72 | *3.48 | 64 |
| *3.28 | 41 | 3.41 | 5 | 3.40 | 6 |
| *3.18 | 100 | *3.29 | 40 | *3.28 | 40 |
| *3.07 | 70 | *3.19 | 100 | *3.18 | 100 |
| 3.00 | 12 | *3.07 | 78 | *3.07 | 70 |
| *2.91 | 87 | 3.01 | 10 | 3.01 | 11 |
| 2.86 | 6 | *2.92 | 96 | *2.91 | 71 |

TABLE 7-continued

| | XRD patterns of dried samples | | | | |
|---|---|---|---|---|---|
| EC-19 | | Comparative Example O | | Example 17 | |
| d(Å) | Relative Intensity | d(Å) | Relative Intensity | d(Å) | Relative Intensity |
| 2.83 | 6 | 2.84 | 8 | 2.86 | 7 |
| 2.79 | 11 | 2.62 | 30 | 2.84 | 7 |
| 2.73 | 2 | 2.55 | 3 | 2.79 | 11 |
| 2.67 | 23 | 2.51 | 20 | 2.67 | 20 |
| 2.65 | 56 | 2.48 | 23 | 2.65 | 48 |
| 2.62 | 31 | 2.43 | 20 | 2.62 | 33 |
| 2.55 | 6 | 2.42 | 15 | 2.55 | 4 |
| 2.50 | 17 | 2.38 | 3 | 2.50 | 16 |
| 2.47 | 22 | 2.30 | 10 | 2.47 | 21 |
| 2.43 | 20 | 2.28 | 15 | 2.43 | 18 |
| 2.41 | 13 | 2.20 | 44 | 2.41 | 12 |
| 2.37 | 3 | 2.15 | 3 | 2.30 | 10 |
| 2.35 | 3 | 2.12 | 2 | 2.27 | 12 |
| 2.30 | 12 | 2.04 | 9 | 2.20 | 36 |
| 2.27 | 13 | 2.01 | 3 | 2.15 | 3 |
| 2.20 | 37 | | | 2.12 | 3 |
| 2.12 | 4 | | | 2.04 | 8 |
| 2.04 | 10 | | | 2.01 | 4 |
| 2.00 | 5 | | | | |

$\frac{\text{Sum peak heights}}{\text{Quartz peak heights}}$

| 0.33 | 0.31 | 0.44 |

$100 \times \frac{\text{(Zeolite 220 + 221) peak areas}}{\text{Quartz 110 peak area}}$

| 15 | 146 | 164 |

I claim:

1. A process for the preparation of a zeolite having an x-ray diffraction pattern obtained from CuK$_\alpha$ radiation with the significant d values set out in Table A hereinbefore and comprising highly crystalline crystallites having at least 50% of its crystallites in the form of distinct circular cylinders with a mean diameter of at least 0.5 micron and an aspect ratio of at least 0.5, in which process an alkaline reaction mixture consisting essentially of water, a source of silicon consisting essentially of a colloidal suspension of silica and a source of aluminum and having a composition (expressed in the mole ratios of oxides) of:

$M_{2/n}O/SiO_2 = 0.22-0.36$ $H_2O/M_{2/n}O = 25-90$ $SiO_2/Al_2O_3 = 5.7-7.4$ (wherein M is a cation of valence n) is heated to a temperature of from at least 75° C. to form the said cylindrical zeolite L.

2. A process as claimed in claim 1, in which M is potassium (K) or a mixture of K+M' in which M' is an alkali metal other than potassium, provided that the molar ratio $K_2/M'_2O+K_2O$ is at least 0.7.

3. A process as claimed in claim 1, in which the reaction mixture is heated to a temperature of at least 100° C.

4. A process as claimed in claim 1, in which the temperature is from 100° to 250° C.

5. A process as claimed in claim 4, in which the temperature is from 120° to 225° C.

6. A process as claimed in claim 1, in which the reaction mixture has the composition:

$M_{2/n}O/SiO_2 = 0.24-0.30$ $H_2O/M_{2/n}O = 35-65$ $SiO_2/Al_2O_3 = 5.7-7.4$.

7. A process as claimed in claim 6, in which the reaction mixture has the molar composition:

$(2.4-3.0)K_2O:(0.6-1.25)Al_2O_3:(8-12)SiO_2:(120-240)H_2O$.

8. A process as claimed in claim 1, in which the relative proportions of aluminium, water, silicon and potassium in the reaction mixture (measured as wt% of the oxides) are such that the reaction mixture falls within area I$_A$ in FIG. 1, area I$_B$ in FIG. 2, area I$_C$ in FIG. 3 and area I$_D$ in FIG. 4, and the reaction mixture is heated to from 120° to 225° C.

9. A process as claimed in claim 8, in which the reaction mixture falls within area II$_A$ in FIG. 1, area II$_B$ in FIG. 2, area II$_C$ in FIG. 3 and area II$_D$ in FIG. 4.

10. A process as claimed in claim 9, in which the reaction mixture falls within area III$_A$ in FIG. 1, area III$_B$ in FIG. 2, area III$_C$ in FIG. 3 and area III$_D$ in FIG. 4.

11. A process as claimed in claim 1, in which the mole ratio of $H_2O/(M_{2/n}O+Al_2O_3+SiO_2)$ is greater than 8.

12. A process according to claim 1 in which the crystallization temperature is about 150° C. and the crystallization time is about 24 to 96 hours.

13. A process according to claim 1 in which the crystallization temperature is greater than 200° C. and the crystallization time is about 8-15 hours.

14. A process according to claim 1 which is carried out in a sealed autoclave at autogenous pressure.

15. A process for the preparation of zeolite having an x-ray diffraction pattern obtained from CuK$\alpha$ radiation with the significant d values set out in Table A hereinbefore and comprising highly crystalline crystallites having at least 50% of its crystallites in the form of disc-shaped circular cylinders with a mean diameter of at least 0.5 micron and an aspect ratio of less than 0.5, in which, an alkaline reaction mixture consisting essentially of water, a source of silicon consisting essentially of a colloidal suspension of silica, a source of aluminum and a source of potassium and having a composition (expressed in mole ratios of oxides) of:

$M_{2/n}O/SiO_2 = 0.20-0.25$ $H_2O/M_{2/n}O = 30-60$ $SiO_2/Al_2O_3 = 35-60$ (wherein M is a cation of valence n) is heated to a temperature of at least 75° C. to form said zeolite.

16. A process according to claim 15 where the synthesis gel composition has the following mole ratios:

$16K_2O:Al_2O_3:4SiO_2:640H_2O$.

17. A process according to claim 15 where the temperature is about 120° C. to 225° C.

18. A process according to claim 17 where the temperature is about 150° C.

19. The product by the process of claim 15.

20. The product by the process of claim 16.

21. A zeolite having an x-ray diffraction pattern obtained from CuK$_\alpha$ radiation with significant d values set out in Table A hereinbefore and comprising highly crystalline crystallites having at least 50% of its crystallites in the form of distinct circular disc-shaped cylinders with an aspect ratio of less than 0.5 and with a mean diameter of at least 0.5 micron.

22. A zeolite according to claim 21 having at least 70% of its crystallites as cylinders.

23. A zeolite according to claim 21 wherein the crystallites have a mean diameter of from 0.5 to 4 microns.

24. A catalyst comprising a zeolite having an x-ray diffraction pattern obtained from $CuK_\alpha$ radiation with significant d values set out in Table A hereinbefore and comprising highly crystalline crystallites having at least 50% of its crystallites in the form of distinct circular disc-shaped cylinders with an aspect ratio of less than 0.5 and with a mean diameter of at least 0.5 micron and a catalytically-active metal.

25. A catalyst according to claim 24 in which the catalytically-active metal is or includes platinum.

26. A catalyst according to claim 25 comprising 0.4 to 1.2 wt% platinum.

27. A catalyst according to claim 24 in which the zeolite is in the potassium form.

* * * * *